United States Patent
Smith

(10) Patent No.: US 10,617,313 B2
(45) Date of Patent: Apr. 14, 2020

(54) PRESSURE CATHETER DEVICE

(71) Applicant: Clinical Innovations, LLC, Murray, UT (US)

(72) Inventor: Steven Smith, Draper, UT (US)

(73) Assignee: Clinical Innovations, LLC, Murray, UT (US)

(*) Notice: Subject to any disclaimer, the term of this patent is extended or adjusted under 35 U.S.C. 154(b) by 319 days.

(21) Appl. No.: 15/243,253

(22) Filed: Aug. 22, 2016

(65) Prior Publication Data

US 2018/0049658 A1    Feb. 22, 2018

(51) Int. Cl.
*A61B 5/03* (2006.01)
*A61B 5/00* (2006.01)
(Continued)

(52) U.S. Cl.
CPC .......... *A61B 5/035* (2013.01); *A61B 5/6853* (2013.01); *A61B 5/6875* (2013.01); *A61M 25/10* (2013.01); *A61B 5/03* (2013.01); *A61B 5/036* (2013.01); *A61B 2562/18* (2013.01); *A61M 25/0102* (2013.01); *A61M 2025/0003* (2013.01);
(Continued)

(58) Field of Classification Search
CPC .......... A61B 5/03; A61B 5/033; A61B 5/035; A61B 5/036; A61B 5/6853; A61B 5/6875; A61B 2562/18; A61M 25/005; A61M 25/10; A61M 25/001; A61M 2025/0003; A61M 2025/1093; A61M 2205/3331; A61M 25/0102; A61M 2025/0004; A61M 2025/0681
See application file for complete search history.

(56) References Cited

U.S. PATENT DOCUMENTS 4,136,681 A  *  1/1979  Hon ..................... A61B 5/035
                                                          600/561
5,566,680 A     10/1996  Urion et al.
(Continued)

FOREIGN PATENT DOCUMENTS

EP         2241347 A2      10/2010
WO     2010141500 A1      12/2010

OTHER PUBLICATIONS

International Search Report for PCT Application No. PCT/US2017/045768 dated Feb. 13, 2018, 7 pages.
(Continued)

*Primary Examiner* — Devin B Henson
(74) *Attorney, Agent, or Firm* — TraskBritt

(57) ABSTRACT

An intrauterine pressure-sensing catheter for detecting pressure changes within the uterus of a patient is disclosed having a tube with a primary lumen extending from a proximal end to a distal end of the elongate tube. A monitor lumen is positioned within the elongate tube between the primary lumen and a wall of the elongate tube and extends from a proximal end of the elongate tube to a distal end of the elongate tube. A pressure-compliant balloon is disposed about an exterior of the elongate tube adjacent a distal end tip. A sleeve is slidably mounted on an exterior of the elongate tube and disposed over the pressure-compliant balloon during insertion of the pressure-sensing catheter within the patient. The distal end tip is configured to prevent movement of the sleeve over the tip and is further configured to provide a zone of protection for the pressure-compliant balloon.

18 Claims, 4 Drawing Sheets

(51) Int. Cl.
*A61M 25/10* (2013.01)
*A61M 25/00* (2006.01)
*A61M 25/01* (2006.01)
*A61M 25/06* (2006.01)

(52) U.S. Cl.
CPC ............ *A61M 2025/0004* (2013.01); *A61M 2025/0681* (2013.01); *A61M 2025/1093* (2013.01); *A61M 2205/3331* (2013.01); *A61M 2210/1433* (2013.01)

(56) References Cited

U.S. PATENT DOCUMENTS

| | | |
|---|---|---|
| 5,573,007 A | 11/1996 | Bobo, Sr. |
| 5,681,344 A | 10/1997 | Kelly |
| 5,951,497 A | 9/1999 | Wallace et al. |
| 5,984,879 A | 11/1999 | Wallace et al. |
| 6,231,524 B1 | 5/2001 | Wallace et al. |
| 6,447,462 B1 | 9/2002 | Wallace et al. |
| 7,065,394 B2 | 6/2006 | Hobot et al. |
| 8,192,368 B2 | 6/2012 | Woodruff et al. |
| 8,790,300 B2 * | 7/2014 | Tun ............... A61B 18/02 604/101.02 |
| 2004/0116955 A1 | 6/2004 | Foltz et al. |
| 2004/0225257 A1 * | 11/2004 | Ackerman ............ A61M 25/10 604/96.01 |
| 2006/0178692 A1 | 8/2006 | Condrea et al. |
| 2008/0300571 A1 | 12/2008 | LePivert |
| 2013/0184612 A1 | 7/2013 | Quackenbush et al. |

OTHER PUBLICATIONS

Written Opinion of the International Searching Authority for PCT Application No. PCT/US2017/045768 dated Feb. 13, 2018, 13 pages.

* cited by examiner

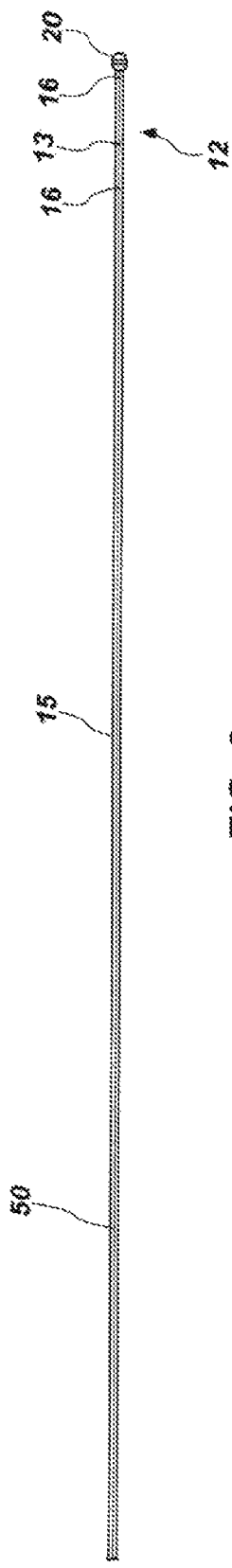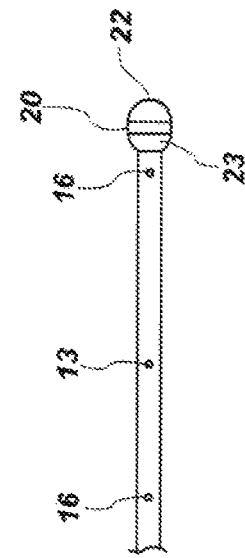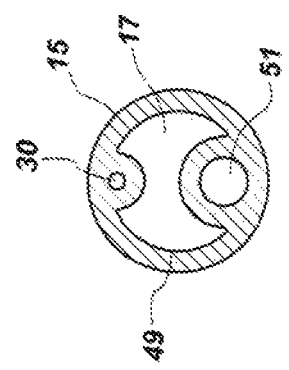

PRESSURE CATHETER DEVICE

TECHNICAL FIELD

Technology embodiments relate generally to medical devices and, more particularly, to devices used for improved advancement of catheters into a body cavity and further to improved use of pressure catheters within the body.

BACKGROUND

The procedure of monitoring and analyzing uterine contractions, during both pregnancy and labor, yields significant information concerning the condition of the unborn child as well as the advancement of labor. Such a procedure is useful during both routine and difficult pregnancies (e.g., those that have increased risk to the health of the child), to systematically evaluate fetal stress. The monitoring procedure is also used when labor is induced. Information indicating distress during pregnancy, labor, and delivery will prompt remedial action, including caesarean delivery, which may save the child from harm and even death. Thus, contraction frequency, duration, intensity, and resting tone are now monitored as part of accepted, standard, obstetrical procedure.

One example of a sensing element used to assess stress is a tocodynamometer or tocotransducer. Tocodynamometers can sense uterine activity externally and non-invasively. The advantages offered by those devices have caused them to be widely used with fetal monitors. Tocodynamometers measure the hardness of the abdominal wall, which is an indication of uterine activity. The tocodynamometer is held adjacent to the patient's abdomen, usually by a belt-like device, in the vicinity of the fundus (the top of the uterus). The tocodynamometer is initialized by setting the recording level so that it is about 10-15 mmHg between contractions. The output of the device is transmitted to the fetal monitor through a pressure transducer, the transducer converting the pressure change information received from the tocodynamometer to an electrical signal that it delivers to the fetal monitor. While externally applied devices like tocodynamometers can provide sufficient information to enable a physician to treat the mother and child during labor and delivery, such devices may suffer large measurement errors, particularly when the environment has extraneous noise or the mother moves extensively. Therefore, a physician may want to have more accurate measurements than can be obtained using external monitoring devices, especially in those childbirth cases involving an elevated risk of complication.

To obtain more reliable and accurate information about the mother's uterine contractions, a physician will often invoke intrauterine pressure monitoring. Intrauterine devices provide information about the frequency, duration, intensity, and resting tone of the uterine contractions. More important, intrauterine devices reduce measurement errors relative to external devices because the uterine pressure is measured directly. However, intrauterine pressure-monitoring devices cause significant discomfort when inserted into the patient, are cumbersome to work with, result in inaccurate or difficult-to-obtain measurements, and/or are potentially dangerous in that the distal ends may dislodge while inside the patient and/or may perforate the uterus or amniotic sac.

BRIEF DESCRIPTION OF THE DRAWINGS

Invention embodiments will become more fully apparent from the following description and appended claims, taken in conjunction with the accompanying drawings. It is to be understood that these drawings merely depict exemplary invention embodiments and are not to be considered limiting of the disclosure's scope. It will be readily appreciated that the components of the embodiments, as generally described and illustrated in the figures herein, could be arranged and designed in a wide variety of different configurations. Nonetheless, the technology will be described and explained with additional specificity and detail through the use of the accompanying drawings in which:

FIG. 2 is a side view of a portion of a catheter in accordance with one aspect of the technology;

FIG. 3a is a side view of a distal end of a catheter in accordance with one aspect of the technology:

FIG. 4 is a cross-sectional view of a catheter in accordance with one aspect of the technology;

DETAILED DESCRIPTION

Figure 1:
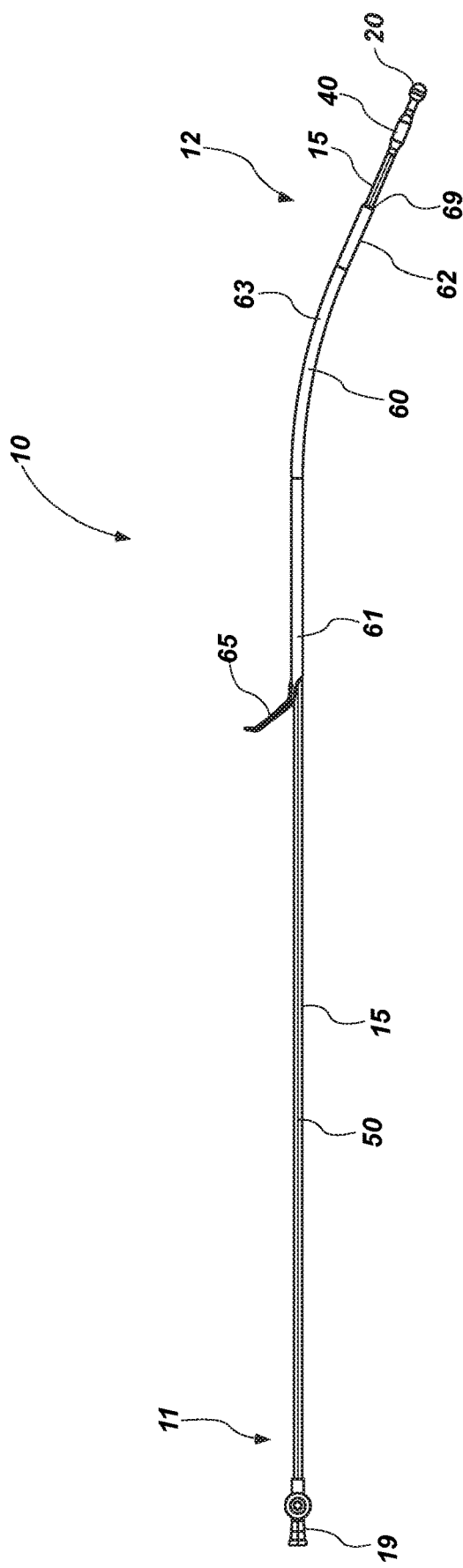
FIG. 1 is a perspective view of a catheter in accordance with one aspect of the technology.

The following detailed description includes reference to the accompanying drawings, which form a part hereof and in which are shown, by way of illustration, exemplary embodiments. It is believed that catheters that utilize improved distal end designs in conjunction with innovative material designs and attendant components improve the performance of the catheter. However, before the present technology is disclosed and described, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting. Although the following detailed description contains many specifics for the purpose of illustration, a person of ordinary skill in the art will appreciate that many variations and alterations to the following details can be made and are considered to be included herein. Accordingly, the following embodiments are set forth without any loss of generality to, and without imposing limitations upon, any claims set forth. Unless defined otherwise, all technical and scientific terms used herein have the same meaning as commonly understood by one of ordinary skill in the art to which this disclosure belongs.

As used in this written description, the singular forms "a," "an" and "the" include express support for plural referents unless the context clearly dictates otherwise. Thus, for example, reference to "a line" includes support for a plurality of such lines.

The term "fluid" used herein refers both to compressible fluids (gases, such as air, etc.) and non-compressible fluids (liquids, such as saline, etc.).

The terms "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term, like "comprising" or "including," in this written description it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein.

The term "coupled," as used herein, is defined as directly or indirectly connected in a fluidic or non-fluidic manner.

Objects described herein as being "adjacent to" each other may be in physical contact with each other, in close proximity to each other, or in the same general region or area as each other, as appropriate for the context in which the phrase is used.

Occurrences of the phrase "in one embodiment," or "in one aspect," herein do not necessarily all refer to the same embodiment or aspect.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about." For example, for the sake of convenience and brevity, a numerical range of "about 50 angstroms to about 80 angstroms" should also be understood to provide support for the range of "50 angstroms to 80 angstroms."

As used herein, a plurality of items, structural elements, compositional elements, and/or materials may he presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 1.5, 2, 2.8, 3, 3.1, 4, 4.6, and 5, individually.

This same principle applies to ranges reciting only one numerical value as a minimum or a maximum. Furthermore, such an interpretation should apply regardless of the breadth of the range or the characteristics being described.

As used herein, "enhanced," "improved," "performance-enhanced," "upgraded," "improvement," and the like, when used in connection with the description of a device, component, or process, refers to a characteristic of the device, component or process that provides measurably better form, function, or outcome as compared to previously known devices or processes. This applies both to the form and function of individual components in a device or process, as well as to such devices or processes as a whole.

Reference throughout this specification to "an example" means that a particular feature, structure, or characteristic described in connection with the example is included in at least one embodiment. Thus, appearances of the phrase "in an example" in various places throughout this specification are not necessarily all referring to the same embodiment.

In addition, the term "catheter" as used herein refers to an elongate tube configured to be inserted into a body cavity. The term "intrauterine catheter" refers to a specific catheter configured for insertion in a mammalian uterus.

EXAMPLE EMBODIMENTS

It should be understood that the aspects of the technology discussed herein are contemplated for use with any type of catheter wherein measurement of pressure within the body of a patient is desired. For purposes of illustrating the various aspects of the methods and systems claimed herein, the discussion below will be primarily directed to describing exemplary embodiments directed to intrauterine pressure sensing. It should be noted, however, that the elements and principles discussed herein are applicable to other applications. It is also noted that discussion of methods and systems herein can be interchangeable with respect to specific aspects. In other words, specific discussion of one method or system (or components thereof) herein is equally applicable to other aspects as they relate to the system or method, and vice versa.

An initial overview of technology embodiments is provided below and specific technology embodiments are then described in further detail. This initial summary is intended to aid readers in understanding the technology more quickly, but is not intended to identify key or essential technological features, nor is it intended to limit the scope of the claimed subject matter. In particular, an elongate catheter is provided having at least one gas-filled pressure-monitoring lumen extending longitudinally through the catheter. A gas-filled membrane (e.g., a balloon) is formed on the outer surface of the catheter near a distal end of the catheter. The gas-filled membrane is in fluid communication with the gas-filled pressure-monitoring lumen. Changes in pressure against the gas-filled membrane will result in changes in pressure of the gas within the gas-filled pressure-monitoring lumen. A pressure transducer is connected to the proximal end of the gas-filled pressure-monitoring lumen to sense and display or record the changes in pressure, which are communicated through the gas-filled pressure-monitoring lumen of the catheter.

When inserted within the uterus, the system allows a medical practitioner to monitor pressure changes within the uterus of a mammalian subject. During high risk pregnancies, the amount of pressure exerted on a child within the uterus of the mother is important to assess the health of the child. In one aspect the device is placed into the amniotic space during labor in order to measure the strength of uterine contractions. External tocodynamometers are used to measure tension across the abdominal wall and detect contraction frequency and duration. However, the appearance of contractions by external monitoring may be affected not only by contraction strength but also by maternal habitus, position, gestational age, and monitor location on the abdomen. Intrauterine pressure catheters work by directly measuring pressure within the amniotic space, which allows for quantification of contraction strength, among other things. With an intrauterine pressure catheter in place, Montevideo units (MVUs) can be calculated to assess for adequacy of labor in cases of suspected labor dystocia or during labor induction. In one aspect, MVUs are calculated by subtracting the baseline uterine pressure from the peak uterine pressure of each contraction in a 10-minute window of time and then taking the sum of these pressures.

Currently available products suffer from a number of deficiencies. For example, currently available catheters are made of stiff materials (e.g., Pellethane or other thermoplastic polyurethane elastomers) that result in significant discomfort during placement and use of the catheter. These stiff materials also adopt a curvilinear "set" or semi-permanent curvature during storage, which encumbers the placement process resulting in frustration to the medical practitioner, suboptimal hygiene, and/or difficulties in placement of the catheter within the uterus. That is, during placement of the catheter, it is critical that the distal end be properly manipulated to avoid extra-ovular placement or other misplacement within the uterus. If the distal end is not straight, the likelihood of misplacement is increased. In addition, a bend in the medial portion of the catheter positions the proximal end of the catheter askew from the remainder of the catheter. As a result the proximal end of the catheter may move about the face of the practitioner, about the anus of the patient, or other areas about the patient that result in hygiene problems while trying to insert the distal end of the catheter into the patient. Additional discomfort is encountered during placement of the catheter within the uterus if components of the catheter that are designed to slidably interact with one another become encumbered requiring more repositioning and/or more forceful placement. Additionally, components with abrupt edges located on the distal end of the catheter cause extreme discomfort during advancement into the uterus and/or result in impingement of the balloon while in the uterus.

In one aspect of the technology, an "oversized" tip is located on the distal end of the catheter. The tip is formed from the catheter tubing itself in order to avoid a loss of the tip within the patient during a procedure. The tip is sized and shaped to minimize encumbrances with abrupt edges associated with a sleeve or introducer and also to provide a "fluid wedge" or "tissue wedge" about the balloon in order to improve operational efficiency. In addition, the catheter comprises a flexible biocompatible elastomeric material with a shape memory stiffener disposed therein. The elastomeric material is more compliant and more comfortable for the patient. The shape memory stiffener is biased in a linear configuration to maintain the linear characteristics of the catheter after it is removed from a curved storage configuration. It also provides the stiffness required to advance the catheter into the patient.

While specific reference is made herein to use of the catheter in connection with intrauterine applications, aspects of the technology can be employed with catheters used for other purposes including, but without limitation, intracranial pressure monitoring, anorectal monitoring, or other medical procedures where the use of a catheter is desired. Reference is also made herein to an apparatus or device. However, it is understood and one or more parts referenced herein may comprise an assembly sold in a sterilized pouch. Individual parts may be sold separately and assembled later while still falling within the scope of the technology described herein.

As shown in FIGS. 1-4, a pressure-monitoring catheter 10 (also referred to as "pressure-sensing catheter") is disclosed comprising an elongate flexible hollow tube 15 that is connectable to a pressure-sensing apparatus by way of connector 19. A data/power cable (not shown) or wireless transmitter (not shown) connects the pressure-sensing catheter to a processor and monitor and/or database. The distal end 12 of the pressure-monitoring catheter 10 comprises a tip 20 that facilitates proper insertion of the pressure-monitoring catheter 10 into the patient. The tip 20 is formed directly from the hollow tube 15, which extends from the tip 20 at its distal end 12 to one or more male connectors 19 (or female connectors, based on a particular design) on its proximal end 11. A plurality of holes or apertures 16 are formed through the wall of the hollow tube 15 behind the tip 20. The number of holes 16 may vary and can be distributed about the circumference of the outer hollow tube 15 and longitudinally about a distal end 12 of the pressure-monitoring catheter 10 to allow fluid to be aspirated or otherwise collected from the patient or infused or delivered in the patient during a procedure. A plurality of holes 16 may be provided so that if any one or more holes 16 should become clogged or blocked, other holes 16 will be available for allowing passage of fluid. The holes 16 are in fluid communication with a primary or central lumen 17 of the hollow tube 15. In an alternative aspect, slits, such as slit valves may be formed through the wall of the outer hollow tube 15 to provide for infusion and/or aspiration of fluids. In one aspect of the technology, the primary lumen 17 has a hydraulic diameter ranging from about 0.75 to about 1.75 mm with one nonlimiting exemplary diameter of 1.1 mm. In one aspect, the hollow tube 15 is coupled to a connector 19. The connector 19 is used to attach a syringe or other device used for the collection (e.g., aspiration) or delivery (e.g., infusion) of fluids to or from the cavity of the patient through holes 16 at the distal end 12 of the pressure-monitoring catheter 10. It is also used to "charge" the catheter as described more fully below.

Figure 3B:
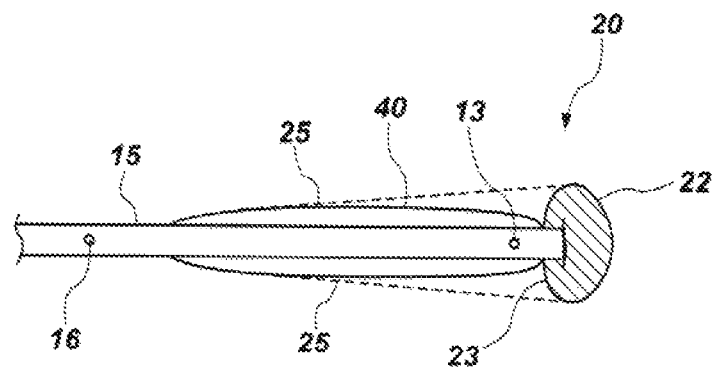
FIG. 3b is a front side view of a distal end of a catheter in accordance with one aspect of the technology.

One or more pressure lumens 30 (also referred to as "monitor lumens") are disposed within the hollow tube 15, as shown more fully in FIG. 4. The pressure lumen 30 extends from the male connector 19, to which it is sealed, to the distal end 12 of the pressure-monitoring catheter 10. The pressure (or monitor) lumen 30 extends from the hollow tube 15 of the pressure-monitoring catheter 10 body to the male connector 19. In one aspect, the monitor lumen 30 is hollow and comprises one or more flexible, biocompatible materials and is integrally formed from or with the sidewall of the hollow tube 15. The pressure or monitor lumen 30 is sized in diameter to fit within the hollow tube 15 and to leave adequate space for passage of fluids through primary or central lumen 17. A flaccid, pressure-compliant member (e.g., a balloon, gel pack, etc.) 40 is in fluid communication with the secondary pressure lumen 30 and is positioned about the hollow tube 15. The pressure-compliant member 40, which is air-filled in one aspect of the technology, is structured to deflect or deform upon application of a force thereto (e.g., an increase in pressure within the body cavity from the contraction of tissues within the body), and to expand again upon removal of the force therefrom (e.g., a subsequent decrease in pressure after a relaxation of the contracting tissues). Therefore, a particularly suitable pressure-compliant member 40 can be a medical grade balloon formed of a thin-walled, flexible, low durometer material such as C-Flex® elastomer, which is relatively easily deformed with a small increase in pressure. As shown in FIGS. 1 and 3b, the pressure-compliant member 40 may be formed as a substantially circular (though other shapes may be used) body that is disposed about and attached to an opening 13 of the pressure (or monitor) lumen 30 and that is heat-sealed at the ends of the pressure-compliant member 40. Air occupies the interior of the pressure lumen 30 and, in one aspect of the technology, is at atmospheric pressure prior to use of the pressure-monitoring catheter 10.

The pressure lumen 30 and the pressure-compliant member 40 attached to the pressure lumen 30 (including any portion of the pressure lumen 30 that extends within the male connector 19) may, therefore, form or define an air column that extends from inside the male connector 19 to near the tip 20 of the pressure-monitoring catheter 10. When the pressure-monitoring catheter 10 is attached to female connector, the air column becomes filled, or "charged," with an additional quantity of air. The additional air charged into the air column partially fills the pressure-compliant member 40 to a selected volume. The material of the pressure-compliant member 40 is very pliant due to its thin wall and the low durometer material used in its construction, and the pressure-compliant member 40 deforms easily, and substantially without artifact introduced by the material of the pressure-compliant member 40 itself, with a given change in pressure external to the pressure-compliant member 40. The material of the pressure-compliant member 40 may, for example, be about a 30 Shore A durometer hardness. Regardless of the material employed, less than 5 mmHg of maximum external pressure should be required to collapse the pressure-compliant member 40 when its interior is vented to atmospheric pressure, though the pressure-compliant member 40 is designed to be operable at pressure ranges ranging from 5 mmHg to 200 mmHg though it can detect pressures from 0 mmHg up to 200 mmHg. The collapse of pressure-compliant member 40, before charging the air column as described, provides an accurate pressure signal. The pressure-compliant member 40 may he attached to an end of the pressure or monitor lumen 30 in any appropriate manner. In one aspect, the pressure-compliant member 40 may be secured by laser welding, adhesive bonding, RF welding, induction welding, hot air welding, or other suitable methods for securing the pressure-compliant member 40 to the pressure-monitoring catheter 10.

In one aspect of the technology, the internal volume of the pressure-compliant member 40 ranges from about 90 µL to about 120 µL with one non-limiting exemplary volume of 100 µL. In one aspect, the diameter of the pressure (or monitor) lumen 30 ranges from about 0.15 to about 0.35 mm with one non-limiting exemplary diameter of 0.25 mm. Based on an exemplary total length of the secondary pressure lumen 30 of 20 cm to 90 cm, the total volume of fluid within the secondary pressure lumen 30 ranges from about 25 µL to about 40 µL with one non-limiting exemplary volume being 32 µL. A charge volume (i.e., the amount of fluid introduced into the air column) ranges from about 40 µL to about 60 µL with one non-limiting exemplary volume of 50 µL. The total volume of the air (or fluid) column is defined by the volume of the pressure (or monitor) lumen 30 and the interior chamber defined by the pressure-compliant member 40 (i.e., the pressure-compliant member 40 volume). Accordingly, in one aspect of the technology, the volume of the air column ranges from about 115 µL to about 160 µL; one non-limiting exemplary volume being 132 µL. As noted herein, the charge volume refers to the total amount of fluid that is introduced into the air (or fluid) column to "charge" or ready the pressure-sensing catheter 10 for pressure measurement. The pressure-monitoring catheter 10 is detachably attached to a cable assembly that is structured to be coupled (either wired or wirelessly) to a processor and monitor. In one aspect where the cable assembly comprises a wired reusable assembly, the reusable interface cable assembly has, at its proximal end, an electrical connector configured to be connected to a processor and a monitor. In the aspect where the cable assembly is wirelessly coupled to a processor and/or monitor, the proximal end of the cable assembly comprises a wireless transmitter.

In one aspect of the technology, the elongate flexible hollow tube 15 comprises an extruded thermoplastic, an elastomer, or a combination of the two having an outside diameter ranging from about 0.09 to about 0.13 inches (i.e., about 2 mm to about 3.5 mm). In one aspect of the technology, the elongate flexible hollow tube 15 comprises a copolymer such as a polyethylene co-vinyl acetate selected from a group consisting of about 60% polyethylene and about 40% vinyl acetate, about 65% polyethylene and about 35% vinyl acetate, about 70% polyethylene and about 30% vinyl acetate, about 75% polyethylene and about 25% vinyl acetate, about 80% polyethylene and about 20% vinyl acetate, and about 85% polyethylene and about 15% vinyl acetate. In one non-limiting example, the hollow tube 15 comprises 81.5% polyethylene and 18.5% co-vinyl acetate. The elongate flexible hollow tube 15 may also comprise a polyethylene co-vinyl acetate having a molecular weight ranging from about 55,000 to about 75,000. In another aspect, the polyethylene co-vinyl acetate has a molecular weight ranging from the about 25,000 to about 250,000. In another aspect, the polyethylene co-vinyl acetate has a molecular weight ranging from the about 85,000 to about 125,000.

While specific reference is made herein to a polyethylene co-vinyl acetate, it is understood that other materials may be used as suits a particular design. For example, C-FLEX®, SANTOPRENE®, silicone, or low-density urethanes may be used. Additional examples include copolymers comprising poly(butylmethacrylate) (PBMA), polycaprolactone (PCL), cellulose acetate, cellulose acetate proprionate, cellulose butyrate, cellulose proprionate, cellulose valerate, cumaroneindene polymer, dibutylaminohydroxypropyl ether, ethyl cellulose, ethylene-vinyl acetate copolymer, glycerol distearate, hydroxypropylmethyl cellulose phthalate, a 2-methyl-5-vinylpyridine methylate-methacrylic acid copolymer, a polyamino acid, a polyanhydride, polybutadiene, a polyester, an aliphatic polyester, polyhydroxybutyric acid, polymethyl methacrylate, polymethacrylic acid ester, a polyolester, a polysaccharide, a protein), vinylchloride-propylene-vinylacetate copolymer, palmitic acid, stearic acid, behenic acid, hyaluronic acid, heparin, keratin sulfate, starch, polystyrene, polyvinyl acetal diethylamino acetate, polyvinyl alcohol, polyvinyl butyral polyvinyl formal, poly (D,L-lactide), poly(D,L-lactide-co-glycolide), poly(glycolide), a poly(orthoglycolide), a poly(orthoglycolide acrylate), a poly(ortho acrylate), a poly(hydroxybutyrate), a poly(alkylcarbonate), a poly(orthoester), poly(hydroxyvaleric acid), polydioxanone, poly(malic acid), poly(tartronic acid), a polyanhydride, or a polyphosphazene.

The modulus of elasticity of the hollow tube 15 may range from about 50 MPa to about 300 MPa and the may have a hardness ranging from about 15 Shore D to about 45 Shore D and a tensile strength ranging from about 2.5 to 7.5 MPa. In addition, the hollow tube 15 by itself may have a flexural modulus ranging from about 50 MPa to about 55 MPa. In any event, the hollow tube 15 comprises a flexible material that is not prone to "set" or assume a particular shape when coiled together in a sealed, sterilized package waiting to be used by a medical practitioner. The final product is malleable, resulting in greater comfort to the patient. It is also collapsible resulting in the ability to be maneuvered through tight spaces with less patient discomfort. It is also lubricious resulting in increased ease of insertion within the patient and a decreased likelihood of being encumbered by a sleeve (or introducer) disposed about an exterior of the hollow tube 15. Moreover, the material should be capable of being melted and molded to form the integral distal end of tip 20 discussed herein.

In one aspect of the technology, in an effort to provide appropriate stiffness to advance the catheter within the patient, an elongate stiffening member 50 is disposed within a stiffening lumen 51 formed within the side wall 49 of hollow tube 15. It has a modulus of elasticity ranging from 30 GPa to 40 GPa, a tensile strength ranging from 850 MPa to 950 MPa and is also resistant to "setting" or assuming a shape when disposed in a curvilinear orientation for an extended period of time. Conventional stiffening members (e.g., steel) adopt a bend when positioned in a coiled or curvilinear configuration for extended periods of time. In one aspect, the present stiffening lumen 51 comprises a shape memory alloy that is biased in a linear configuration.

Shape memory alloys ("SMAs") are a unique class of metal alloys that can recover apparent permanent strains when they are heated above a certain temperature and also exhibit pseudoelastic properties. Unlike the conventional use of a shape memory alloy that is biased in a curvilinear arrangement and configured to bend into a linear arrangement or other curvilinear arrangement, stiffening lumen 51 is biased to stay in a linear arrangement when subject to temperatures outside of the body and also when it encounters temperatures typical for the inside of a mammalian subject. In other words, the stiffening members are predisposed to resist. In this manner, the stiffening lumen 51 provides rigidity to the pressure-monitoring catheter 10 without the drawback of adopting a curvilinear "set" after being stored in a curved or coiled arrangement for extended periods of time. In one aspect, the stiffening lumen 51 comprises an alloy selected from a group consisting of nickel-titanium, copper-aluminum-nickel, copper-zinc-aluminum, and iron-manganese-silicon. In one aspect of the technology, the shape memory alloy comprises nickel, titanium and from about 3 atomic percent (hereinafter at. %) to about 20 at. %, based on the weight of the total weight of the alloy composition, of at least one additional element selected from the group consisting of niobium, hafnium, tantalum, tungsten and gold. However, other alloys that have a similar function are contemplated for use herein (e.g., gold-cadmium, polymer-based alloys, etc.). In one aspect of the technology, the flexural modulus of the combined hollow tube 15 and stiffening lumen 51 is orders of magnitude (at least one) greater than the hollow tube 15 itself providing the appropriate amount of stiffness to the pressure-monitoring catheter 10.

In one aspect of the technology, the catheter comprises an introducer or sleeve 60 disposed about an exterior of the hollow tube 15 configured to slide about a longitudinal axis of the hollow tube 15. The sleeve 60 is sized such that an inner diameter of the sleeve 60 is slightly larger than the outer diameter of the hollow tube 15. In this manner, it is capable of sliding about a longitudinal axis of the hollow tube 15. Generally speaking, the sleeve 60 comprises a thermoplastic material that is more rigid than the hollow tube 15 and is intended to assist the medical practitioner in placing the distal end 12 of pressure-monitoring catheter 10 within the patient. In one aspect of the technology, a proximal end 61 of sleeve 60 is substantially straight or linear and a distal end 62 of the sleeve 60 is substantially straight or linear. A medial portion 63 of the sleeve 60 is curvilinear. The overall curvature of sleeve 60 is important in certain applications (e.g., intrauterine insertion) as it optimizes placement within body cavities with unique geometries, such as the vaginal canal. The exact location of the curve within the sleeve 60 may vary depending on a particular design of the sleeve 60. In one aspect of the technology, the curve is placed closer to the distal end 62 of sleeve 60 as shown in the drawings. However, the curve may he located in the middle of the sleeve or closer to the proximal end 61 of the sleeve 60. Use of conventional stiffeners in connection with the curved sleeve 60 is suboptimal because the conventional stiffener will adopt a curvilinear shape during storage of the device prior to use. As noted above, the use of a SMA (e.g., Nitinol, etc.) as a stiffener biased in a linear configuration provides an elastic property to the stiffener. Thus, because the elongate stiffening member 50 holds a linear configuration even after storage in a curved orientation, the distal end 12 of pressure-monitoring catheter 10 remains linear during insertion within the patient minimizing the likelihood of improper placement within the body cavity (e.g., extra-ovular placement, etc.).

In one aspect of the technology, the proximal end 61 of the sleeve 60 comprises a tab 65 configured to be held between the thumb and index finger of a medical practitioner during placement of the pressure-monitoring catheter 10 within the body. In one aspect, the tab 65 is substantially oval and has a plurality of ridges 66 extending across the face (or front side) 67 of the tab 65. In another aspect, the tab 65 has a plurality of ridges disposed about its back side 68. In one aspect, after the cervix of the patient is adequately dilated, the distal end 12 of the pressure-monitoring catheter 10 (located within the sleeve 60) is inserted just through the cervix into the amniotic space. Once the distal end 12 of pressure-sensing catheter 10 (together with the distal end 62 of the introducer or sleeve 60) is appropriately positioned, the practitioner's examining hand holds the introducer 60 in place while the other hand is used to advance the pressure-monitoring catheter 10 through the sleeve 60 into the amniotic space about 10-12 cm. The pressure-monitoring catheter 10 should move easily into the amniotic space. With correct placement, clear or blood-tinged fluid will be seen within the primary lumen 17 of the pressure-monitoring catheter 10. If blood or no fluid returns, the pressure-monitoring catheter 10 is likely located between the membranes and endometrium (extra-ovular), and it should be withdrawn and repositioned. Once correct position is confirmed, the pressure-sensing catheter 10 is farther advanced until a "stop" marking on the pressure-monitoring catheter 10 is located at the vaginal introitus. The introducer or sleeve 60 is then removed while the pressure-monitoring catheter 10 is held in place to prevent its inadvertent removal. In one aspect of the technology, the sleeve 60 comprises a channel or opening 70 extending across a longitudinal axis of the sleeve 60. The channel 70 allows the user to remove the sleeve 60 from the pressure-monitoring catheter 10 after it is introduced into the cervix (or other body cavity). When the procedure is over, the pressure-monitoring catheter 10 should be easily removed by simply pulling gently on the pressure-monitoring catheter 10. Occasionally, the pressure-monitoring catheter 10 does not advance easily through the introducer 60 or may be felt coiling just past the cervix. This may occur because the pressure-monitoring catheter 10 is being blocked by a part of the child, is encumbered by the sleeve 60, or because the pressure-monitoring catheter 10 (or any associated stiffener) has taken on a curved orientation during storage within the sleeve. Aspects of the technology described herein minimize these encumbrances.

In one aspect of the technology, the distal end of tip 20 of pressure-monitoring catheter 10 is formed and sized such that its outer diameter is greater than an outer diameter of the pressure-monitoring catheter 10 itself, and/or of the sleeve 60, particularly the distal end 62 of sleeve 60 and/or the pressure-compliant member 40. In this manner, when the sleeve 60 is abutted against the back side 23 of tip 20, it cannot be advanced over the tip 20. Advantageously, the sleeve 60 and tip 20 will not become encumbered reducing the ability of the pressure-monitoring catheter 10 to easily slide within the sleeve 60. In other words, it will not make it difficult for the practitioner to advance the pressure-monitoring catheter 10 further into the patient after the sleeve 60/pressure-monitoring catheter 10 assembly has been properly positioned within the cervix. Moreover, while advancing the sleeve 60/pressure-monitoring catheter 10 assembly within the cervix, the sleeve 60 exerts a directional force against the tip 20 that is parallel with a longitudinal axis of pressure-monitoring catheter 10. This ensures that the sleeve 60/pressure-monitoring catheter 10 assembly is jointly advanced within the patient in parallel. In one aspect, the practitioner can advance the pressure-monitoring catheter 10 into the body cavity using only one hand because there is no need to worry about advancing the pressure-monitoring catheter 10 and sleeve 60 simultaneously. Rather, the directional force of the sleeve 60 exerted on the back side 23 of tip 20 ensures that the pressure-monitoring catheter 10 and sleeve 60 are uniformly advanced. In one non-limiting example, the tip 20 has an outer diameter of 0.25 inches (i.e., about 6.5 mm) and the sleeve 60 has an outer diameter of 0.23 inches (i.e., about 5.8 mm). The tip 20 also assists the user in detecting extra-ovular placement due to the difference in diameters between the tip 20 and the hollow tube 15. That is, the practitioner will have an enhanced ability to sense extra-ovular placement due to the ratio of the diameter of the tip 20 to the diameter of the hollow tube 15.

In one aspect of the technology, the distal end of tip 20 is dome-shaped or hemispherical (e.g., FIG. 3b). That is, a face (or front side) 22 of the tip 20 is rounded or curvilinear and a back side 23 is substantially flat or planar. In another aspect of the technology, the tip 20 comprises a "mushroom" shape. That is, the face 22 of the tip 20 has a substantially flat surface tapering to a narrower back side 23 (e.g., FIG. 3c). In other words the distal end of tip 20 comprises a first diameter about a front side 22 of the distal end tip and a second diameter about a back side 23 of the distal end of tip 20; the first diameter being greater than the second diameter. In any event, when the sleeve 60 is abutted against a back side 23 of tip 20 (e.g., FIG. 3c), the outside diameter of tip 20 is greater than the outside diameter of the sleeve 60 effectively preventing the sleeve 60 from sliding over the tip 20 of pressure-monitoring catheter 10. As noted above, when advancing a prior art sleeve/catheter arrangement in the body, the sleeve may push over or become wedged about the tip of the catheter. However, with the tip 20 of the present technology, this encumbrance is minimized. In addition, the abrupt edges 69 of the distal end 62 of sleeve 60 do not push against any tissues of the patient as the arrangement is advanced within the body because the abrupt edges 69 are located behind, and contained within, the outer perimeter of the face or front side 22 of tip 20. Because the tip 20 is made from a relatively softer material, patient comfort is greatly improved by removing contact between the abrupt edges 69 and the patient tissues.

Figure 3C:
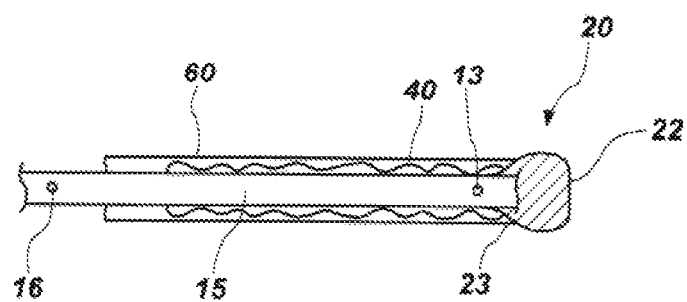
FIG. 3c is a side view of a distal end of a catheter in accordance with one aspect of the technology.
Figure 5A:
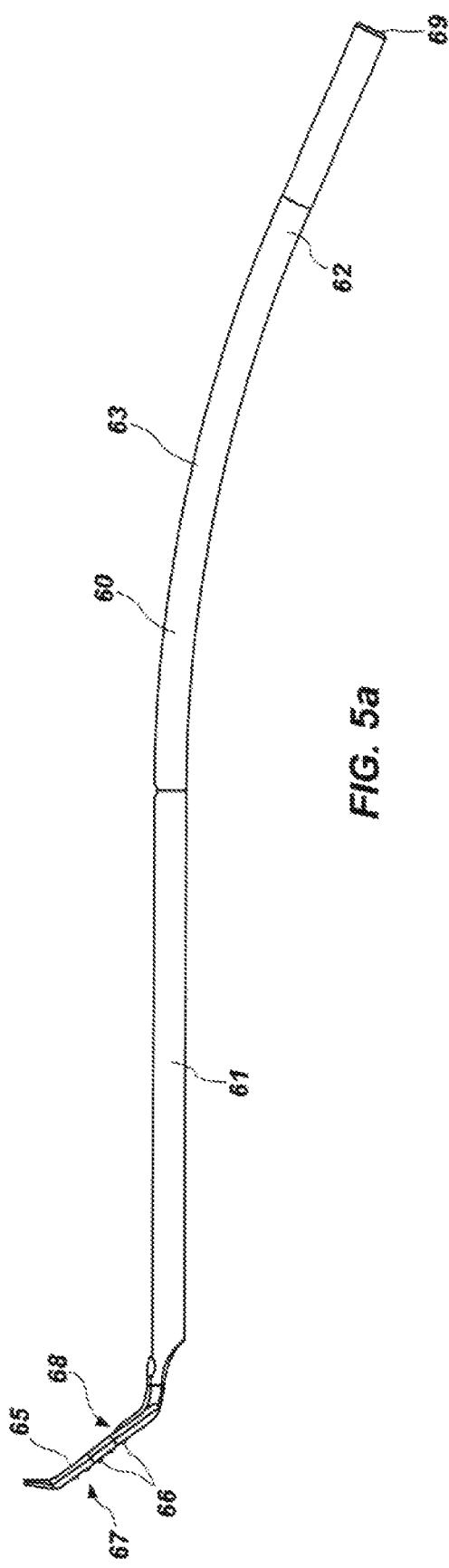
FIG. 5a is a side view of a sleeve in accordance with one aspect of the technology.
Figure 5B:
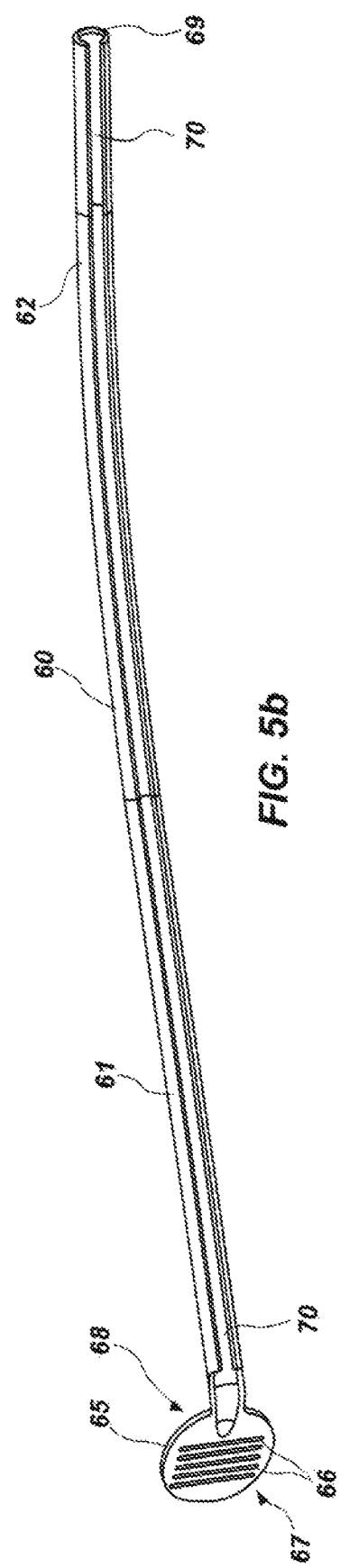
FIG. 5b is a bottom view of a sleeve in accordance with one aspect of the technology.

With reference to FIG. 3b, in one aspect of the technology, the pressure-compliant member 40 is located adjacent the tip 20 of pressure-monitoring catheter 10. While the pressure-compliant member 40 is covered by sleeve 60 during advancement of the device into the body (as shown in FIG. 3c), the sleeve 60 is removed as the pressure-monitoring catheter 10 is advanced further into the body after initial placement. Thus, the pressure-compliant member 40 is exposed so that a pressure reading may be taken within the body as discussed herein. In some instances, parts of the child or patient tissue may impinge upon the pressure-compliant member 40 making it difficult to obtain pressure readings from the device. The tip 20 has an outer diameter that is greater than an outer diameter of the pressure-compliant member 40 and, in one aspect of the technology, is placed adjacent the pressure-compliant member 40 on the distal end 12 of pressure-monitoring catheter 10. In this manner, the tip 20 creates a protective wedge 25 where tissue will not encumber the pressure-compliant member 40.

Advantageously, the protective wedge 25 reduces tissue impingement upon the pressure-compliant member 40, instead allowing the area within the protective wedge 25 to fill with fluid. The result is an increased ability to obtain pressure readings within the relative cavity of the body. The precise geometry and placement of the tip 20 with respect to the pressure-compliant member 40 will determine the size and geometry of the protective wedge 25. In one aspect, when "charged," the pressure-compliant member 40 has an outer diameter of about 0.22 inches (i.e., about 5.6 mm) and a longitudinal length of 0.7 inches (about 17.8 mm). In an aspect where the outer diameter of the tip 20 ranges from about 0.2 to about 0.3 inches (i.e., about 5 mm to about 7.6 mm), it is believed that a protective wedge 25 will extend the longitudinal distance of the pressure-monitoring catheter 10. A larger outer diameter of the pressure-compliant member 40 will result in a longer protective wedge 25. While the pressure-compliant member 40 is described as being adjacent the tip 20, it may be located anywhere about the longitudinal length of the pressure-monitoring catheter 10 within the length of the protective wedge 25 and still enjoy the benefit of the protective wedge. Thus, a relatively short pressure-compliant member 40 can have a greater range about the longitudinal axis of the pressure-monitoring catheter 10 where it may be placed with a larger tip 20 or can be paired with relatively small tip 20 while still falling within the protective wedge 25. The different shaped tips 20 contemplated herein likewise effect the longitudinal length of protective wedge 25. Moreover, while the protective wedge 25 will not preclude rigid or semi-rigid encumbrances from the area about the pressure-compliant member 40, pliable and soft tissue will be precluded from immediately obstructing the area within the protective wedge 25.

In one aspect of the technology, the tip 20 is formed by pushing the distal end 12 of the hollow tube 15 into a cup-shaped heating element and melting the hollow tube 15 itself. The hollow tube 15 is advanced into the cup of the heating element, the outer walls of the hollow tube 15 the melt and fold over the outside of the walls immediately behind the melted distal end. In this aspect, the cup-shaped element is sized to approximate the shape of a dome or a hemisphere wherein the diameter of the hemisphere is sized to approximate the desired size of the tip 20. In this manner, as the hollow tube 15 is advanced into the cup, the melted tubing fills the cup and conforms to the desired shape and size. In this aspect, the tip 20 is substantially solid. That is, at least the front side 22 of the tip 20 is not collapsible and does not contain any hollow portions. Moreover, because the pressure-monitoring catheter 10 is configured to detect pressure within the pressure-compliant member 40, the tip 20 is free from any mechanical accoutrements, including, for example, a pressure transducer or other catheter related machinations. Depending on a specific design, the back side 23 of the tip 20 may have a hollow portion as it molds about the distal end 12 of the hollow tube 15. While specific reference is made herein to a hemisphere (e.g., FIG. 3b), it is understood that the tip 20 may comprise other three-dimensional shapes, including, hut without limitation, an ellipsoid (e.g., FIG. 3a), a frustum, or other shapes.

In one aspect of the technology, the tip 20 is substantially symmetrical about its axis that is collinear with a longitudinal axis of the pressure-sensing catheter 10 and particularly the distal end 12 of catheter 10. Reference is made herein to a protective wedge 25 created by tip 20 about the pressure-compliant member 40. In an aspect where the pressure-compliant member 40 is symmetrical about a longitudinal axis of the catheter 10, the tip 20 is likewise symmetrical in order to create a symmetrical protective wedge 25 about the pressure-compliant member 40. In an aspect where a pressure-sensing element disposed within the protective wedge 25 is asymmetrically disposed about the distal end 12 of pressure-monitoring catheter 10, the tip 20 may not be symmetric, though it may be symmetric as suits a particular catheter design, desire for patient comfort, and ease of manufacturing, for example. Moreover, asymmetric tip is difficult to rotate within a body cavity when attempting to reposition the catheter to gain or regain a signal. When the tip is lodged in a small space (e.g., between the uterus and the baby, etc.) will "sandwich" an asymmetric tip resulting in skewed data. The ability to rotate a symmetrical tip in any axial position allows the practitioner more flexibility during a procedure.

The foregoing detailed description describes the technology with reference to specific exemplary embodiments. However, it will be appreciated that various modifications and changes can be made without departing from the scope of the present disclosure as set forth in the appended claims. The detailed description and accompanying drawings are to be regarded as merely illustrative, rather than as restrictive, and all such modifications or changes, if any, are intended to fall within the scope of the present disclosure as described and set forth herein.

More specifically, while illustrative exemplary invention embodiments have been described herein, the disclosure is not limited to these embodiments, but includes any and all embodiments having modifications, omissions, combinations (e.g., of aspects across various embodiments), adaptations and/or alterations as would be appreciated by those skilled in the art based on the foregoing detailed description. The limitations in the claims are to be interpreted broadly based on the language employed in the claims and not limited to examples described in the foregoing detailed description or during the prosecution of the application, which examples are to be construed as non-exclusive. For example, in the present disclosure, the term "preferably" is non-exclusive where it is intended to mean "preferably, but not limited to." Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the disclosure should be determined solely by the appended claims and their legal equivalents, rather than by the descriptions and examples given above.

What is claimed is:

1. An intrauterine pressure-sensing catheter for detecting pressure within the uterus of a patient comprising:
    an elongate tube comprising a primary lumen extending from a proximal end of the elongate tube to a distal end of the elongate tube;
    a monitor lumen positioned within the elongate tube, the monitor lumen extending between the proximal end of the elongate tube and the distal end of the elongate tube;
    a pressure-compliant balloon defining an interior chamber in fluid communication with the monitor lumen, the pressure-compliant balloon being disposed about an exterior of the elongate tube, the monitor lumen and the interior chamber of the pressure-compliant balloon in combination defining a fluid column;

a sleeve slidably mounted over the exterior of the elongate tube and positioned over the pressure-compliant balloon during insertion of the pressure-compliant balloon of the pressure-sensing catheter within at least the cervix of the patient; and an integral distal end tip formed from material of the elongate tube and located adjacent to the pressure-compliant balloon, the distal end tip comprising an outer diameter that is greater than an outer diameter of the sleeve, a rounded front and a back extending substantially transverse to a longitudinal axis of the elongate tube, wherein the distal end tip is symmetric about an axis of the tip corresponding to a longitudinal axis of the elongate tube, and wherein a diameter of the distal end tip is equal to or greater than a diameter of the pressure-compliant balloon when inflated.

2. The pressure-sensing catheter of claim 1, wherein the sleeve comprises a linear proximal end, a linear distal end and a curvilinear medial portion, and is configured to slide longitudinally along the elongate tube.

3. The pressure-sensing catheter of claim 2, wherein a proximal end of the sleeve comprises an oval tab configured to be held between the thumb and index finger of a medical practitioner during placement of the pressure-compliant balloon of the pressure-sensing catheter within the body, wherein a face of the tab comprises a plurality of ridges extending across the face of the tab.

4. The pressure-sensing catheter of claim 2, wherein during placement of the pressure-compliant balloon of the pressure-sensing catheter within the uterus of the patient, a distal end of the sleeve is abutted against a back end of the distal end tip.

5. The pressure-sensing catheter of claim 1, wherein the distal end tip comprises a first diameter about a front side of the distal end tip and a second diameter about a back side of the distal end tip, wherein the first diameter is greater than the second diameter.

6. The pressure-sensing catheter of claim 1, wherein an outer surface of the distal end tip tapers from a first diameter to a second diameter.

7. The pressure-sensing catheter of claim 1, further comprising an elongate stiffening member disposed within a secondary lumen of the elongate tube and extending within the secondary lumen between the proximal end of the elongate tube and the distal end of the elongate tube, the stiffening member being biased in a linear configuration.

8. The pressure-sensing catheter of claim 7, wherein the stiffening member comprises a shape memory alloy selected from the group consisting of nickel-titanium, copper-aluminum-nickel, copper-zinc-aluminum, and iron-manganese-silicon.

9. A pressure-sensing catheter for detecting pressure within a cavity of a patient, comprising:

an elongate hollow tube comprising a primary lumen extending between a proximal end of the elongate hollow tube and a distal end of the elongate hollow tube, the elongate hollow tube comprising a polyethylene co-vinyl acetate;

a monitor lumen positioned within the elongate hollow tube, said monitor lumen extending between a proximal end of the elongate hollow tube and a distal end of the elongate hollow tube and in fluid communication with a pressure-compliant balloon on an exterior of the elongate hollow tube;

a sleeve disposed about the exterior of the elongate hollow tube, the sleeve having a linear proximal portion, a linear distal portion and a curvilinear medial portion, the sleeve being slideable about a longitudinal axis of the elongate hollow tube and positioned over the pressure-compliant balloon during insertion of the pressure-compliant balloon of the pressure-sensing catheter within at least the cervix of the patient;

a stiffening member comprising a shape memory alloy disposed within a secondary lumen of the elongate hollow tube and extending between the distal end of the elongate hollow tube and the proximal end of the elongate hollow tube, wherein the stiffening member is biased in a linear configuration; and an integral distal end tip located adjacent to the pressure-compliant balloon, the distal end tip comprising a rounded front and a back extending substantially transverse to a longitudinal axis of the elongate hollow tube, wherein the distal end tip is symmetric about an axis of the tip corresponding to a longitudinal axis of the elongate hollow tube, and wherein a diameter of the distal end tip is equal to or greater than a diameter of the pressure-compliant balloon when inflated.

10. The pressure-sensing catheter of claim 9, wherein the elongate hollow tube comprises a polyethylene co-vinyl acetate selected from the group consisting of about 60% polyethylene and about 40% vinyl acetate, 65% polyethylene and about 35% vinyl acetate, 70% polyethylene and about 30% vinyl acetate, and about 75% polyethylene and about 25% vinyl acetate.

11. The pressure-sensing catheter of claim 9, wherein the elongate hollow tube comprises a polyethylene co-vinyl acetate having a molecular weight ranging from about 55,000 g/mol to about 75,000 g/mol.

12. The pressure-sensing catheter of claim 9, wherein the elongate hollow tube comprises a material having a modulus of elasticity ranging from about 50 MPa to about 200 MPa, has a durometer ranging from about 15 Shore D to about 45 Shore D, and has a flexural modulus ranging from about 50 MPa to about 55 MPa.

13. The pressure-sensing catheter of claim 12, wherein the flexural modulus of the combined elongate hollow tube and shape memory alloy stiffening member disposed within the elongate hollow tube is at least an order of magnitude greater than the flexural modulus of the hollow tube by itself.

14. The pressure-sensing catheter of claim 9, wherein the elongate hollow tube of the pressure-sensing catheter comprises an outside diameter ranging from about 0.09 to about 0.13 inch and wherein the distal end tip comprises an outside diameter ranging from about 0.2 to about 0.3 inch.

15. The pressure-sensing catheter of claim 9, further comprising a female connector removably attached to a male connector, the male connector coupled to the proximal end of the elongate hollow tube in communication with the monitor lumen and the female connector coupled to a data cable, wherein the female connector comprises a pressure sensor configured to transmit a signal to a processor, the signal corresponding to a change in pressure in the pressure-compliant balloon sensed by the pressure sensor.

16. A method of detecting pressure within the cavity of a body, comprising:

advancing a distal end of a pressure-sensing catheter/sleeve assembly into a body cavity, the pressure-sensing catheter comprising: a monitor lumen positioned within a primary lumen and extending between a proximal end of the pressure-sensing catheter and a distal end of the pressure-sensing catheter, the monitor lumen in fluid communication with a pressure-compliant balloon disposed on a distal end of the pressure-sensing catheter adjacent a distal end tip, the distal end tip being formed from material of the distal end of the pressure-sensing catheter, being substantially solid and comprising an outer diameter greater than an outer diameter of the pressure-compliant balloon after the pressure-compliant balloon is charged and inflated with a volume of air, and a stiffener disposed in a secondary lumen of the catheter, wherein the sleeve is disposed adjacent the distal end tip and over the pressure-compliant balloon during advancement of the assembly into the body cavity;

advancing the pressure-sensing catheter through the sleeve further into the body cavity;

removing the sleeve from the body cavity;

removing the sleeve from the pressure-sensing catheter;

propagating a volume of air through the monitor lumen into the pressure-compliant balloon to charge and inflate the pressure-compliant balloon;

detecting a change of pressure acting on the pressure-compliant balloon; and removing the pressure-sensing catheter from the body cavity.

17. The method of claim 16, wherein the pressure-sensing catheter comprises a polyethylene co-vinyl acetate and the stiffener comprises a shape memory alloy.

18. The method of claim 16, wherein detecting a change of pressure is effected using a pressure sensor coupled to a proximal end of the pressure-sensing catheter and in fluid communication with the monitor lumen.

* * * * *